US008668640B2

(12) United States Patent
MacAulay et al.

(10) Patent No.: US 8,668,640 B2
(45) Date of Patent: Mar. 11, 2014

(54) METHODS AND APPARATUS FOR IMAGING USING A LIGHT GUIDE BUNDLE AND A SPATIAL LIGHT MODULATOR

(75) Inventors: Calum E. MacAulay, Vancouver (CA); Andrew L. P. Dlugan, Surrey (CA); Pierre Lane, Vancouver (CA)

(73) Assignee: Motic China Group Co., Ltd., Xiamen (CN)

(*) Notice: Subject to any disclaimer, the term of this patent is extended or adjusted under 35 U.S.C. 154(b) by 1412 days.

(21) Appl. No.: 12/259,232

(22) Filed: Oct. 27, 2008

(65) Prior Publication Data

US 2009/0244272 A1 Oct. 1, 2009

Related U.S. Application Data

(60) Continuation of application No. 12/070,908, filed on Feb. 20, 2008, now abandoned, which is a continuation of application No. 11/811,869, filed on Jun. 11, 2007, now abandoned, which is a continuation of application No. 10/688,783, filed on Oct. 17, 2003, now Pat. No. 7,235,047, which is a division of application No. 09/738,257, filed on Dec. 14, 2000, now Pat. No. 6,663,560.

(60) Provisional application No. 60/172,436, filed on Dec. 17, 1999, provisional application No. 60/192,081, filed on Mar. 24, 2000, provisional application No. 60/244,427, filed on Oct. 30, 2000.

(51) Int. Cl.
*A61B 1/07* (2006.01)
*A61B 1/00* (2006.01)
*G02B 6/06* (2006.01)

(52) U.S. Cl.
CPC ......... *A61B 1/00172* (2013.01); *A61B 1/00165* (2013.01); *A61B 1/07* (2013.01); *G02B 6/06* (2013.01)
USPC ........... 600/182; 600/160; 600/168; 600/181; 385/116; 385/119; 359/298

(58) Field of Classification Search
USPC .......... 600/160, 182, 168, 181; 359/201, 298, 359/368, 233; 385/31, 116, 117, 119; 362/574, 575
See application file for complete search history.

(56) References Cited

U.S. PATENT DOCUMENTS

| 4,676,593 A | 6/1987 | Adachi et al. |
| 4,802,748 A | 2/1989 | McCarthy et al. |

(Continued)

FOREIGN PATENT DOCUMENTS

| DE | 3108389 A1 | 4/1982 |
| EP | 0022220 A2 | 1/1981 |

(Continued)

OTHER PUBLICATIONS

Nakamura, Osamu et al. "Multispectral Computed-Tomography Microscope for 3-D Material Analysis," Applied Optics. vol. 29, No. 11; 1671-1674 (1990).

(Continued)

*Primary Examiner* — John P Leubecker
(74) *Attorney, Agent, or Firm* — Graybeal Jackson LLP; Joshua King

(57) ABSTRACT

Endoscopes and other viewing devices that control the light that contacts a sample and/or that is detected emanating from a sample. The viewing devices are particularly well suited for in vivo imaging, although other uses are also included. The viewing devices, and methods related thereto, comprise a spatial light modulator in the illumination and/or detection light path so that light transmitted to the target via a bundle of light guides or optical system is transmitted substantially only into the cores of the light guide bundle and not into the cladding surrounding the light guides, filler between the light guides in the bundle, or undesired light guides. Also, methods and apparatus for mapping the pixels of the spatial light modulator to the cores of the light guides in the bundle (preferably at least 3 pixels (e.g., at least 3 mirrors for a digital micromirror device) for each core), as well as for mapping the light guides of one light guide bundle to another.

6 Claims, 6 Drawing Sheets

(56) References Cited

U.S. PATENT DOCUMENTS

| | | | |
|---|---|---|---|
| 5,067,805 | A | 11/1991 | Corle et al. |
| 5,099,363 | A | 3/1992 | Lichtman |
| 5,162,941 | A | 11/1992 | Favro et al. |
| 5,237,403 | A | 8/1993 | Sugimoto et al. |
| 5,430,816 | A | 7/1995 | Furuya et al. |
| 5,514,127 | A | 5/1996 | Shanks |
| 5,587,832 | A | 12/1996 | Krause |
| 5,659,642 | A | 8/1997 | King et al. |
| 5,742,419 | A | 4/1998 | Dickensheets et al. |
| 5,815,624 | A | 9/1998 | Rosenberg |
| 5,867,251 | A | 2/1999 | Webb |
| 5,907,425 | A | 5/1999 | Dickensheets et al. |
| 5,930,027 | A | 7/1999 | Mentzer et al. |
| 6,128,077 | A | 10/2000 | Jovin et al. |
| 6,370,422 | B1 | 4/2002 | Richards-Kortum et al. |
| 6,388,809 | B1 | 5/2002 | MacAulay |
| 6,399,935 | B1 | 6/2002 | Jovin et al. |
| 6,487,351 | B1 | 11/2002 | Cryan et al. |
| 2004/0178329 | A1 | 9/2004 | Kare et al. |

FOREIGN PATENT DOCUMENTS

| | | | |
|---|---|---|---|
| EP | 0482340 | A1 | 4/1992 |
| EP | 1079255 | A2 | 2/2001 |
| JP | 5817403 | | 2/1983 |
| JP | 03134608 | A | 7/1991 |
| WO | 9922262 | | 5/1999 |
| WO | 9940471 | | 8/1999 |
| WO | 9952416 | | 10/1999 |
| WO | 0067060 | | 11/2000 |

OTHER PUBLICATIONS

Kawata, S. et al. "Optical Microscope Tomography. I. Support Constraint," J. Optical Society of America. vol. 4, No. 1; 292-297 (1987).
Nakamura, O. et al. "Optical Microscope Tomography. II. Nonnegative Constraint by a Gradient-Projection Method," Optical Society of America. vol. 5, No. 4; 554-561 (1988).
Kawata, S. et al. "Optical Microscope Tomography," Inverse Optics II. vol. 558; 15-20 (1985).
Kawata, S. et al. "Laser Computed-Tomography Microscope," Applied Optics. vol. 29, No. 26; 3805-3890 (1990).
Dabbs, Tim et al. "Fiber-Optic Confocal Microscope: FOCON," Applied Optics. vol. 31, No. 16; 3030-3035 (1992).
Ginivas, L. et al. "Scanning Fibre-Optic Microscope," Electronic Letters. vol. 27, No. 9; 724-726 (1991).
Ginivas, L. et al. "Endoscope with Optical Sectioning Capability," Applied Optics. vol. 32, No. 16; 2888-2890 (1993).
Dickensheets, D.L. et al. "Micromachined Scanning Confocal Optical Microscope," Optics Letters. vol. 21, No. 10; 764-766 (1996).
Gmitro, Arthur F. et al. "Confocal Microscopy Through a Fiber-Optic Imaging Bundle," Optics Letters. vol. 18, No. 8; 565-567 (1993).
Sabharwal, Yashvinder S. et al. "Slit-Scanning Confocal Microendoscope for High-Resolution in vivo Imaging," Applied Optics. vol. 38, No. 34; 7133-7144 (1999).
Juskaitis, R. et al. "Confocal Microscopy using Optical Fibre Imaging Bundles," SPIE. vol. 2655; 92-94 (1996).
Lane, Pierre M. et al. "Fiber-Optic Confocal Microscopy Using a Spatial Light Modulator," Optics Letters. vol. 25, No. 24; 1780-1782 (2000).
European Patent Office, International Search Report, International Application No. PCT/US00/33880, Jun. 6, 2001, 2 pages.
U.S. Appl. No. 60/244,427, filed Oct. 30, 2000, titled, "Confocal Micodendoscopy Using a Spatial Light Modulator", Inventor: Calum E. MacAulay, 10 pages.

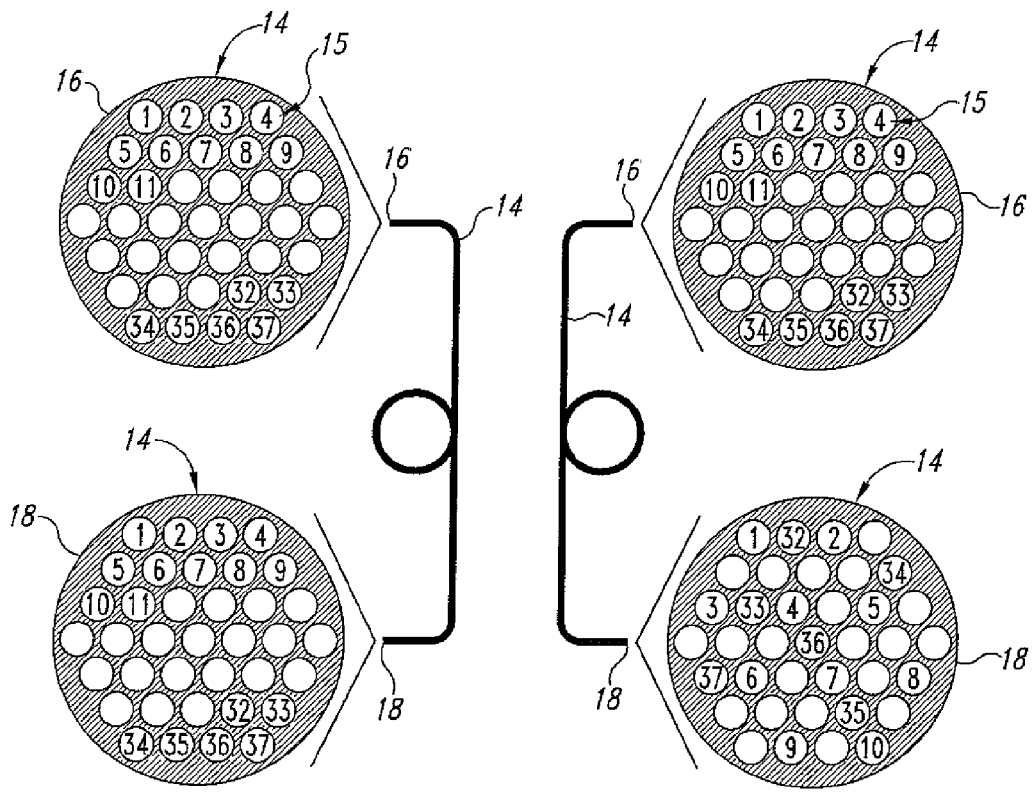
*Fig. 6A*  *Fig. 6B*
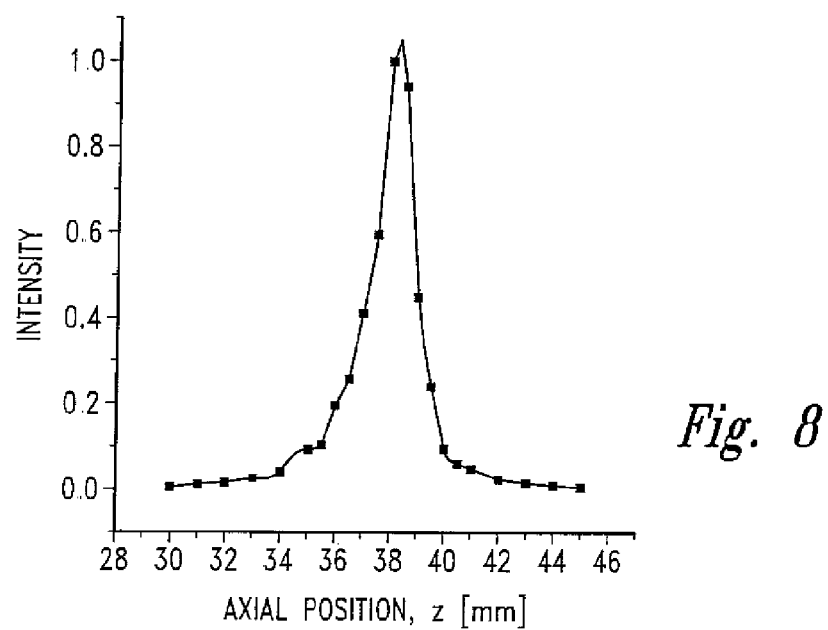
*Fig. 8*

METHODS AND APPARATUS FOR IMAGING USING A LIGHT GUIDE BUNDLE AND A SPATIAL LIGHT MODULATOR

CROSS-REFERENCE TO RELATED APPLICATIONS

The present application is a continuation of U.S. patent application Ser. No. 12/070,908, filed Feb. 20, 2008, which application is a continuation of U.S. patent application Ser. No. 11/811,869, filed Jun. 11, 2007, which application is a continuation of U.S. patent application Ser. No. 10/688,783, filed Oct. 17, 2003, now U.S. Pat. No. 7,235,047, issued Jun. 26, 2007; which application is a divisional of U.S. patent application Ser. No. 09/738,257, filed Dec. 14, 2000, now U.S. Pat. No. 6,663,560, issued Dec. 16, 2003; which claims the benefit under 35 USC §119 of U.S. Provisional Patent Application Ser. No. 60/172,436, filed Dec. 17, 1999; U.S. Provisional Patent Application Ser. No. 60/192,081, filed Mar. 24, 2000; and from U.S. Provisional Patent Application Ser. No. 60/244,427, filed Oct. 30, 2000; all of the foregoing applications are incorporated by reference herein and their entireties.

FIELD OF THE INVENTION

The field of the present invention is imaging using a light guide bundle.

BACKGROUND OF THE INVENTION

Microscopes magnify objects or samples, which can be stationary and moving. One type of microscope is a confocal microscope, which uses a very small spot, or pinhole, of light to make its image of the target. Typically, the spot is scanned across the target in a pointwise, digital fashion and the image is made by combining the points of return light emanating from the target (the return light can be, for example, reflected light, fluorescent light, or an exotic form of light such as a Raman spectrum, and can be found in any desirable region of the electro-magnetic spectrum, such as ultraviolet (UV) light, blue light, visible light, near-infrared (NIR) light and infrared (ER) light).

The confocal geometry of the illumination pinhole, the object, and the detection pinhole give a higher resolution image than a conventional widefield microscope. In some embodiments, confocal microscopy can improve the spatial resolution about 1 3 times. See, e.g., U.S. Pat. No. 5,587,332. Confocal microscopy also improves the "up and down" (i.e., z-axis or axial) resolution, which gives rise to an extremely useful optical sectioning capability; which means that images can be obtained at different depths, and thus 3-D images and volume reconstruction can be obtained.

In order to obtain the pointwise image, confocal microscopes can either move a specimen and keep the optics fixed in place, or they can keep the specimen fixed and move the light beam, for example by scanning the beam using special rotating aperture disks or other beam scanners. See U.S. Pat. No. 4,802,748, U.S. Pat. No. 5,067,805, U.S. Pat. No. 5,099,363, U.S. Pat. No. 5,162,941. Other confocal scanning systems have used a laser beam rastered with rotating mirrors to scan a specimen or a laser beam that scans a slit rather than a spot; such slit scanning increases imaging speed but slightly degrades resolution. See U.S. Pat. No. 5,587,332.

Confocal microscopes typically use a bulky design in which several large components—including a laser system as the light source, detection pinholes, x-y beam steering devices, and an optical detector—must be carefully maintained in precise alignment. In these systems, the specimen or target to be imaged is placed on a stage as in a conventional microscope. These limitations make the confocal microscope cumbersome, inflexible and inconvenient for imaging specimens which are not easily accessible or easily placed on a microscope stage. In other words, present confocal systems are designed for in vitro imaging of biological specimens in the lab instead of imaging tissues in the body, in vivo.

Several approaches have been proposed to permit in vivo imaging. See, e.g., T. Dabbs and M. Glass, "Fiber-optic confocal microscope: FOCON," Applied Optics, vol. 31, pp 3030-3035, 1992; L. Giniunas, R. Juskatis, and S. V Shatalin, "Scanning fiber-optic microscope," Electronic Letters, vol. 27, pp. 724-725, 1991; L. Giniunas, R. Juskatis, and S. V. Shatalin, "Endoscope with optical sectioning capability," Applied Optics, vol 32, pp. 2883-2890, 1993; D. L. Dickensheets and G. S Kino, "Micromachined scanning confocal optical microscope," Optics Letters, vol. 21, pp. 764-766, 1996; D. L. Dickensheets and G. S. Kino, "Miniature scanning confocal microscope,"U.S. Pat. No. 5,907,425 (continuation of 5,742,419), May 1999; A. F. Gmitro and D. Aziz, "Confocal microscopy through a fiber-optic imaging bundle," Optics letters, vol. 18, pp. 565-567, 1993; Y. S. Sabharwal, A. R. Rouse, L. Donaldson, M. F. Hopkins, and A. F. Gmitro, "Slit-scanning confocal microendoscope for high-resolution in vivo imaging, Applied Optics, vol. 38, pp. 7133-7144, 1999; R. Juskaitis, T. Wilson, and I. F. Watson, "Confocal microscopy using optical fibre imaging bundles," Proceedings of SPIE, vol. 2655, pp. 92-94, 1996; U.S. Pat. No. 5,587,832; PCI/CA98/00993, Publication No. WO 99/2.2.262. None of these systems provide as high a quality of image as could be desired for various aspects of microscopy.

Thus, there has gone unmet a need for improved microscopy systems, including confocal microscopy systems, wherein the systems can provide high quality images of desired targets in locations where the positioning of the target might not be carefully controlled, including in vivo targets. The present invention provides these and other advantages.

SUMMARY OF THE INVENTION

The present invention comprises microscopes and methods that have significant advantages in controlling the light that contacts a sample and/or that is detected emanating from a sample. The microscopes and methods, which preferably relate to confocal microscopes and further preferably confocal endoscopes for in vivo imaging, comprise a spatial light modulator in the illumination and/or detection light path so that light transmitted to the target, for example via a bundle of light guides, is transmitted substantially only into the cores of the light guide bundle and not into inter-core areas such as the cladding surrounding the light guides or filler between the light guides in the bundle. This may reduce the amount of noise or stray light in the image from the target tissue, thereby enhancing the sensitivity, contrast or resolution of the image, in at least one of the x-y directions and in the z-direction, and provides other related advantages. The present invention may also provide systems comprising only a single light guide bundle in a microendoscope and can reduce cross-talk between light guides.

In one aspect, the present invention provides a viewing system comprising a spatial light modulator and a light guide bundle having a proximal end and a distal end, wherein spatial light modulator is optically connected to the proximal end of the light guide bundle in a same conjugate image plane as the proximal end such that the spatial light modulator controls the location of light impinging on the proximal end. In some embodiments, the viewing system of comprises an endoscope or the light guide bundle comprises at least 100 light guides. The endoscope can be a confocal microscopy endoscope. The spatial light modulator can be operably connected to a controller comprising computer-implemented programming able to set to an on-state pixels of the spatial light modulator corresponding to cores of corresponding light guides in the light guide bundle to provide on-pixels and able to set to an off-state pixels corresponding to inter-core areas of the light guide bundle to provide off-pixels.

In other embodiments, a plurality of selected groups of the on-pixels are in the on-state, the selected groups being spaced apart such that light emanating from the distal end of a first light guide corresponding to a first selected group of on-pixels does not substantially interfere with light emanating from the distal end of a second light guide corresponding to a second selected group of on-pixels, and substantially all other pixels of the spatial light modulator are in the off-state. Typically, at least 3 different pixels of the spatial light modulator correspond to each core of substantially all of the corresponding light guides. The viewing system can further comprise a pixelated detector optically connected to receive light emanating from the proximal end of the light guide bundle and the controller further comprises computer-implemented programming that distinguishes between light emanating from the light guides corresponding to on-pixels of the spatial light modulator and light emanating from other light guides. The computer-implemented programming can additionally ignores light emanating from the other light guides.

In further embodiments, the controller further comprises computer-implemented programming that detects light emanating from the other light guides to provide out-of-focus data and the programming incorporates the out-of-focus data with the light emanating from the light guides corresponding to the on-pixels to provide an enhanced image. The out-of-focus data can be fit using the light emanating from the light guides corresponding to the on-pixels using a 2D Gaussian distribution or using desired point spread functions as described herein.

The viewing system can be a single-pass or double-pass viewing system, and the viewing system can further comprise a light source optically connected to the proximal end of the light guide bundle and the spatial light modulator is optically connected between the light source and the proximal end of the light guide bundle. Where the viewing system is a double-pass viewing system, and the viewing system can further comprise a light source and a detector that are both optically connected to the proximal end of the light guide bundle, and the spatial light modulator is optically connected between a) each of the light source and the detector, and b) the proximal end of the light guide bundle. In some embodiments, the controller further comprises computer-implemented programming that maps pixels of the spatial light modulator to corresponding cores of corresponding light guides in the light guide bundle to provide a map comprising corresponding pixels and non-corresponding pixels.

The viewing system can further comprise a scanner that controls the location of light transmitted to the spatial light modulator and on to the proximal end of the light guide bundle, and the controller further comprises computer-implemented programming that directs the scanner to scan the spatial light modulator and simultaneously sets at least one of the corresponding pixels to an on-state and sets other pixels of the spatial light modulator to an off-state, thereby causing light horn the light source to be transmitted substantially only to the cores of corresponding light guides. The viewing system can also comprise a light source optically connected to the spatial light modulator such that the light source illuminates a substantial portion of the pixels of the spatial light modulator, and the controller further comprises computer-implemented programming that sets selected corresponding pixels to an on-state and sets other pixels of the spatial light modulator to an off-state, thereby causing light from the light source to be transmitted substantially only to the cores of the light guides corresponding to the corresponding pixels. The controller can further comprise computer-implemented programming that selects the selected corresponding pixels that are set to an on-state such that light emanating from the distal end of a first light guide corresponding to a first selected corresponding pixel does not substantially interfere with light emanating from the distal end of a second light guide corresponding to a second selected corresponding pixel, and the selected corresponding pixels that are set to an on-state are varied over time such that substantially all of the light guides in the light guide bundle are illuminated.

In another aspect, the present invention provides a flexible endoscope system providing confocal microscopy of a target tissue, the system comprising an endoscope comprising a light guide bundle comprising at least 100 light guides and having a proximal end and a distal end, the system further comprising a spatial light modulator that is optically connected to the proximal end of the light guide bundle in a same conjugate image plane as the proximal end such that the spatial light modulator controls the location of light impinging on the proximal end, and a controller comprising computer-implemented programming that is operably connected to the spatial light modulator and that is able to set to an on-state groups of pixels of the spatial light modulator corresponding to cores of corresponding light guides in the light guide bundle to provide groups of on-pixels and able to set to an off-state pixels corresponding to inter-core areas of the light guide bundle to provide off-pixels. A plurality of selected groups of the on-pixels can be in the on-state, the selected groups being spaced apart such that light emanating from the distal end of a first light guide corresponding to a first selected group of on-pixels does not substantially interfere with light emanating from the distal end of a second light guide corresponding to a second selected group of on-pixels, and other pixels of the spatial light modulator are in the off-state.

The endoscope can further comprise a pixelated detector optically connected to receive light emanating from the proximal end of the light guide bundle and the controller further comprises computer-implemented programming that distinguishes between light emanating from the light guides corresponding to on-pixels of the spatial light modulator and light emanating from other light guides.

The present invention also provides methods of making an viewing system comprising: a) providing a spatial light modulator; b) providing a light guide bundle having a proximal end and a distal end; and, c) placing the spatial light modulator in optical connection to the proximal end of the light guide bundle in a same conjugate image plane as the proximal end such that the spatial light modulator controls the location of light impinging on the proximal end. The viewing system can be a confocal microscopy endoscope and the method further comprises providing the light guide bundle comprising at least 100 light guides. The methods can further comprise operably connecting the spatial light modulator to a controller comprising computer-implemented programming able to set to an on-state pixels of the spatial light modulator corresponding to cores of corresponding light guides in the light guide bundle to provide on-pixels and able to set to an off-state pixels corresponding to inter-core areas of the light guide bundle to provide off-pixels.

The methods can further comprise optically connecting a pixelated detector to the system to receive light emanating from the proximal end of the light guide bundle and further providing the controller with computer-implemented programming that distinguishes between light emanating from the light guides corresponding to on-pixels of the spatial light modulator and light emanating from other light guides. The method can be directed to making a single-pass or double-pass viewing system, and can further comprise providing a scanner that controls the location of light transmitted to the spatial light modulator and on to the proximal end of the light guide bundle or optically connecting the light source to the spatial light modulator such that the light source illuminates a substantial portion of the pixels of the spatial light modulator.

The present invention further provides methods of making a flexible endoscope system comprising: a) providing a spatial light modulator; b) providing a light guide bundle comprising at least 100 light guides having a proximal end and a distal end, at least the distal end of the light guide bundle disposed within an endoscope; c) placing the spatial light modulator in optical connection to the proximal end of the light guide bundle in a same conjugate image plane as the proximal end such that the spatial light modulator controls the location of light impinging on the proximal end; and, d) operably connecting a controller comprising computer-implemented programming to the spatial light modulator wherein the controller is able to set to an on-state groups of pixels of the spatial light modulator corresponding to cores of corresponding light guides in the light guide bundle to provide groups of on-pixels and able to set to an off-state pixels corresponding to inter-core areas of the light guide bundle to provide off-pixels. Such methods can further comprise optically connecting a pixelated detector to the system to receive light emanating from the proximal end of the light guide bundle and further providing the controller with computer-implemented programming that distinguishes between light emanating from the light guides corresponding to on-pixels of the spatial light modulator and light emanating from other light guides.

The present invention still further provides methods of illuminating a target comprising: a) transmitting light from a light source to a proximal end of a light guide bundle via a spatial light modulator wherein the spatial light modulator transmits the light substantially only to cores of light guides in the light guide bundle; b) transmitting the light from the proximal end of the light guide bundle to a distal end of the light guide bundle and emitting the light from the distal end of the light guide bundle; and, c) illuminating the target with the light emitted from the distal end of the light guide bundle. The methods can comprise scanning a light beam across the spatial light modulator and simultaneously setting at least one pixel of the spatial light modulator that corresponds to a core of one of the light guides to an on-state to provide at least one on-pixel and setting other pixels of the spatial light modulator to an off-state, whereby the light beam is transmitted substantially only to the core of the light guide when the light beam contacts the on-pixel and the light beam is not transmitted to inter-core areas of the light guide bundle or to light guides adjacent to the light guide. The light beam can be a laser beam or other desired light beam.

In some embodiments, the methods comprise scanning the light beam across substantially all pixels that are set to an on-state over time such that substantially all of the light guides in the light guide bundle are illuminated, thereby illuminating substantially all of the target within a field of view of the light guide bundle without moving the light guide bundle. In further embodiments, the methods comprise optically connecting the light source to the spatial light modulator such that the light source illuminates a substantial portion of the pixels of the spatial light modulator, and setting selected corresponding pixels to an on-state and setting other pixels of the spatial light modulator to an off-state such that light from the light source is transmitted substantially only to the cores of the light guides corresponding to the corresponding pixels. The method can comprise varying the selected corresponding pixels that are set to an on-state over time such that substantially all of the light guides in the light guide bundle are illuminated, thereby illuminating substantially all of the target within a field of view of the light guide bundle without moving the light guide bundle.

The methods can comprise selecting the selected corresponding pixels that are set to an on-state such that light emanating from the distal end of a first light guide corresponding to a first selected corresponding pixel does not substantially interfere with light emanating from the distal end of a second light guide corresponding to a second selected corresponding pixel.

The present invention also provides methods of obtaining an image of a target comprising: a) transmitting light from a light source via a spatial light modulator to a light guide bundle, then emitting the light from a distal end of the light guide bundle to illuminate the target and thereby cause light to emanate from the target to provide emanating light; b) collecting the emanating light that contacts the distal end of the light guide bundle; and c) transmitting the emanating light via the light guide bundle to a detector to provide an image of the target at the detector. The detector can comprise, for example, an eyepiece ocular or a pixelated detector, and the image can be a confocal image.

The methods can comprise setting to an on-state pixels of the spatial light modulator that correspond to cores of corresponding light guides in the light guide bundle to provide on-pixels and setting to an off-state pixels corresponding to inter-core areas of the light guide bundle to provide off-pixels. The methods can also comprise setting a plurality of selected groups of the on-pixels to an on-state wherein the selected groups are spaced apart such that light emanating from the distal end of a first light guide corresponding to a first selected group of on-pixels does not substantially interfere in the target with light emanating from the distal end of at least one second light guide corresponding to at least one second selected group of on-pixels, and substantially all other pixels of the spatial light modulator are in the off-state. The methods can further comprise distinguishing between light emanating from the light guides corresponding to on-pixels of the spatial light modulator and light emanating from other light guides, then ignoring light emanating from the other light guides or evaluating the light emanating from the other light guides to provide out-of-focus data and the incorporating the out-of-focus data with the light emanating from the light guides corresponding to the on-pixels to provide an enhanced image.

The methods can be effected using a single-pass viewing system such that the spatial light modulator acts as an illumination mask such that illumination light is transmitted substantially only to light guide cores of light guides that correspond to on-pixels of the spatial light modulator, or a double-pass viewing system, such that the spatial light modulator acts as an illumination mask such that illumination light is transmitted substantially only to corresponding light guides and as a detection mask that substantially prevents light from light guides other than corresponding light guides from reaching the detector.

The methods can comprise mapping pixels of the spatial light modulator to corresponding cores of corresponding light guides in the light guide bundle to provide a map comprising corresponding pixels and non-corresponding pixels.

These and other aspects, features and embodiments are set forth within this application, including the following Detailed Description and attached drawings. In addition, various references are set forth herein, including in the Cross-Reference To Related Applications, that describe in more detail certain compositions, apparatus, methods and other information (e.g., spatial light modulators, etc.); all such references are incorporated herein by reference in their entirety and for all their teachings and disclosures, regardless of where the references may appear in this application.

BRIEF DESCRIPTION OF THE DRAWINGS

FIG. 6 provides a schematic view of coherent and non-coherent light guide bundles.

FIG. 8 is a graph depicting the axial response of a plane mirror scanned through focus, with a FWHM of 1.6 µm.

DETAILED DESCRIPTION OF THE INVENTION

Figure 1:
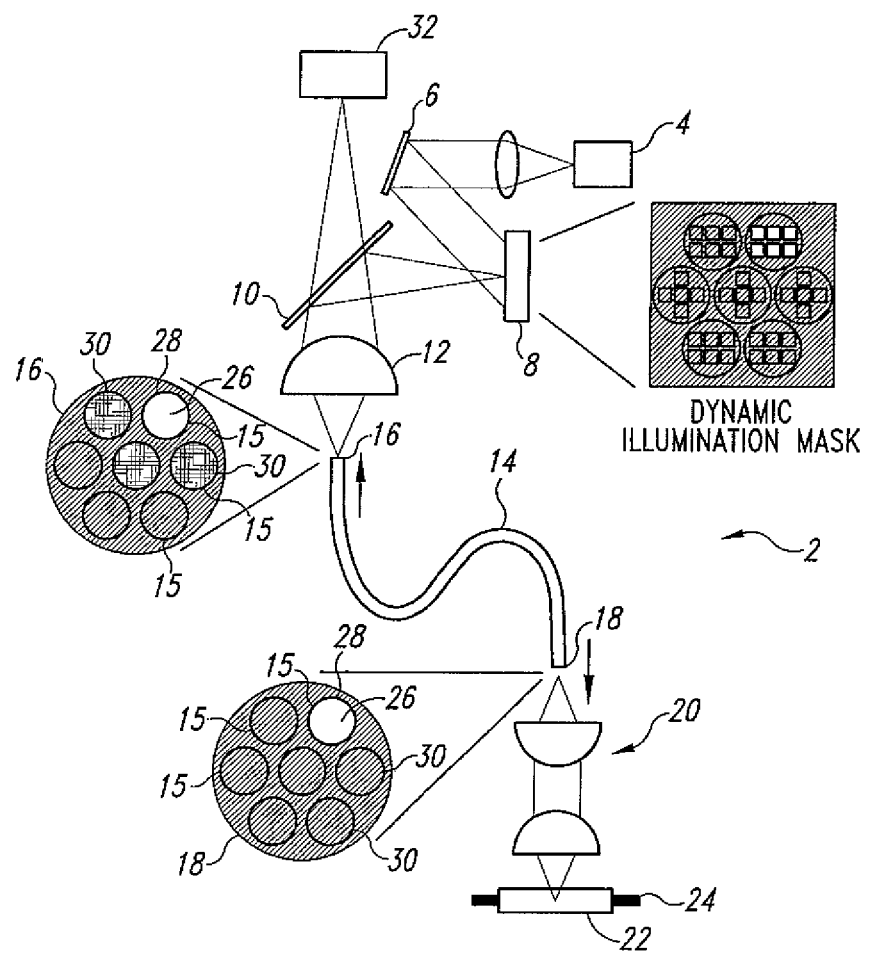
FIG. 1 provides a schematic view with expanded schematic views of a single-pass viewing device comprising a spatial light modulator and a light guide bundle.

The present invention provides endoscopes and other viewing devices that control the light that contacts a sample and/or that is detected emanating from a sample. The viewing devices are particularly well suited for in vivo imaging, although other uses are also included. The viewing devices, and methods related thereto, comprise a spatial light modulator in the illumination and/or detection light path so that light transmitted to the target via a bundle of light guides is transmitted substantially only into the cores of the light guide bundle and not into the cladding surrounding the light guides, filler between the light guides in the bundle, or undesired light guides. This enhances the resolution of the resulting image, laterally and axially directions (figuratively, side to side and up and down), and provides other related advantages. The present invention also provides methods and apparatus, for mapping the pixels of the spatial light modulator to the cores of the light guides in the bundle (preferably at least 3 pixels (e.g., at least 3 mirrors for a digital micromirror device) for each core), as well as for mapping the light guides of one light guide bundle to another.

Definitions

The following paragraphs provide definitions of some of the terms used herein. All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" means "including without limitation" unless expressly stated otherwise).

A "spatial light modulator" (SLM) is a device that is able to selectively modulate light. The present invention comprises one or more spatial light modulators disposed in the light path of a viewing system, generally an image magnification or transmission system such as an endoscope or microscope. Typically, a spatial light modulator comprises an array of individual light transmission pixels, which are a plurality of spots that have transmissive characteristics such that they either transmit or pass the light along the light path or block the light and prevent it from continuing along the light path (for example, by absorbing the light or by reflecting it out of the light path). Such pixelated arrays are well known in the art, having also been referred to as a multiple pattern aperture array, and can be formed by an array of ferroelectric liquid crystal devices, by a digital micromirror device, or by electrostatic microshutters. See, U.S. Pat. No. 5,587,832; R. Vuelleumier, Novel Electromechanical Microshutter Display Device, Proc. Eurodisplay '84, Display Research Conference September 1984 Digital micromirror devices can be obtained from Texas Instruments, Inc, Dallas, Tex., U.S.A. "On pixels" are pixels or optical elements, either individually or in groups, that have been set to an "on-state" and thus to transmit light along the light path between a light source and sample or between a sample and a detector; "off pixels" are pixels that have been set to an "off-state" and thus to transmit light out of such a light path(s).

An "illumination light path" is the light path from a light source to a target or sample, while a "detection light path" is the light path for light emanating from a sample to a detector. Light emanating from a sample includes light that reflects from a sample, is transmitted through a sample, or is created within the sample, for example, Raman spectra or fluorescent light that is created within a sample pursuant to excitation with an appropriate wavelength of light (typically UV or blue light). The illumination and emanating light include ultraviolet (UV) light, blue light, visible light, near-infrared (NIR) light and infrared (IR) light.

An "endoscope" is a device, usually tubular, for insertion into a body, typically via canals, vessels, passageways or body cavities for any of a variety reasons, including surgical and diagnostic purposes, as well as other purposes such as the injection or withdrawal of fluids or to keep a passageway open.

A "light guide" is a device well known in the art, typically flexible, that comprises an outer layer and a light transmissive core that carries light from one location to another, such as an optical fiber, liquid light guide or hollow reflective light guide. The outer layer can comprise the outer surface of the same material that makes up the core or can be a separate or additional material. A light guide typically also comprises a substantially non-light transmissive cladding. A "light guide bundle" is a plurality of such light guides combined into a single strand, and can comprise a binder or filler material between the individual light guides of the bundle. Such cladding and filler, as well as anything else that may be disposed between the light guide cores of a light guide bundle, can be referred to as an inter-core area.

The "proximal end" of a light guide or endoscope is the end of the light guide or endoscope that receives light from light source. The proximal end is typically maintained outside the body, and typically comprises one or more handles, knobs and/or other control devices that allow the user to manipulate the distal end of the endoscope and/or devices located at the distal end of the light guide or endoscope The "distal end" of a light guide or endoscope is the end of the light guide or endoscope that is typically farther away from the light source and thus emits light from the light source that has impinged upon the proximal end of the light guide or endoscope and been transmitted to the distal end. The distal end is, in the case of an endoscope or other in vivo device, the end that is inserted into the body and directed to a target. As used herein, the distal end of the endoscope includes the distal tip of the endoscope, which is the most distal surface or opening of the endoscope, and the portion of the endoscope adjacent to the distal tip of the endoscope.

A "controller" is a device that is capable of controlling a spatial light modulator, a detector or other elements of the apparatus and methods of the present invention. For example, the controller can control the transmissive characteristics of the pixels in a spatial light modulator, control the on/off status of pixels of a pixelated light detector (such as a charge coupled device (CCD) or charge injection device (CID)), and/or compile data obtained from the detector, including using such data to make or reconstruct images or as feedback to control an upstream spatial light modulator. The detector, or other components of the present invention if desired, can also be used with a photomultiplier tube (PMT). Typically, a controller is a computer or other device comprising a central processing unit (CPU) and capable of implementing computer-readable programming such as algorithms and software. Controllers are well known in the art and selection of a desirable controller for a particular aspect of the present invention is within the scope of the art in view of the present disclosure.

"Upstream" and "downstream" are used in their traditional sense wherein upstream indicates that a given device is closer to a light source, while downstream indicates that a given object is farther away from a light source.

A "conjugate image plane of an aperture diaphragm of the objective lens" is a plane in either the illumination or detection light path where an image of the aperture diaphragm of the objective lens is recreated. In a Kohler illumination system, this image plane can also contain a recreation of the image of the light source, which in the present invention can be any light source such as a white light, an arc lamp or a laser The conjugate image planes of the aperture diaphragm of the objective lens define locations that control the angle of illumination light that is ultimately impinged on a sample, as well as the angle of detection light that emanates from a sample (the "angle of illumination" and "angle of detection" refer to the angle of the light that is either impinging upon or emanating from a sample).

A "conjugate image plane of the sample" is a plane in either the illumination light path or the detection light path wherein image of the sample is recreated. The light detector(s) is typically located in one such site in the detection light path. The conjugate image planes of the sample defines locations that can control the size and location of spots on the sample that are illuminated and/or detected (depending upon whether the conjugate plane is in the illumination light path or the detection light path). The image plane of the sample is the plane wherein the sample is located, although the image plane of the sample can be greater or smaller than the size of the actual sample if either a plurality of light paths are provided or if the illumination area is greater or smaller than the size of the sample A "same conjugate image plane" is a plane that is conjugate to another image plane Thus, the multiple locations of the conjugate image planes of an aperture diaphragm of the objective lens are same conjugate image planes, and the multiple locations of the conjugate image plane of the sample are also same conjugate image planes. For example, in some embodiments a spatial light modulator is placed in the same conjugate image plane as the proximal end of the light guide bundle, which is a location that is like the conjugate image plane of the sample and defines locations that can control the size and location of light impinging on the proximal end of the light guide bundle, and thus can control which light guides within the bundle are illuminated and/or detected (depending upon whether the spatial light modulator is in the illumination light path or the detection light path); a light guide that corresponds to (receives light from or emits light to) a pixel or group of pixels of the spatial light modulator in the on-state can be referred to as a "corresponding light guide." An individual light guide may be switched from corresponding to non-corresponding status by switching the pixels from on-state to off-state without moving the individual light guide relative to the spatial light modulator.

The terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim. The present invention comprises multiple aspects, features and embodiments including methods, apparatus, systems and the like; such multiple aspects, features and embodiments can be combined and permuted in any desired manner unless other expressly stated or clear from the context.

Other terms and phrases in this application are defined in accordance with the above definitions, and in other portions of this application.

The Figures

Turning to the FIGS, FIG. 1 provides a schematic view with expanded schematic views of a single-pass viewing system 2 comprising a light source 4 that emits light that reflects off mirror 6 then continues via spatial light modulator 8, beam splitter 10 and objective lens 12 to illuminate the core 26 of a light guide 15, here an optical fiber, in a light guide bundle 14. As demonstrated by the expanded view in FIG. 1, at the distal end 18 of light guide bundle 14 the light illuminates substantially only the core 26 of corresponding light guide 28 but not inter-core area 27 or adjacent light guides 30. The light is then relayed to the target 22 by lens system 20. In FIG. 1, the viewing system 2 is a reflective system, so return light emanates from target 22, which is transmitted back through the viewing system past beam splitter 10 to detector 32, which can be an ocular eyepiece, a pixelated detector or other desired detector. Transmission light microscopes are also included in the present invention. Beam splitter 10 can be a filter that reflects light having a first wavelength, such as light from light source 4, while transmitting light of other wavelengths, such as return light emanating from sample 22.

The viewing system 2 in FIG. 1 is a single-pass viewing system, which means that light passes the spatial light modulator 8 only a single time and thus spatial light modulator 8 is optically connected into only the illumination light path. If desired, one or more additional SLMs can be provided in the illumination light path or the detection light path.

In FIG. 1, spatial light modulator 8 provides an illumination mask. For example, light from light source 4 illuminates a substantial portion of the pixels of spatial light modulator 8, then spatial light modulator 8 provides the illumination mask because a controller (not shown) sets selected pixels corresponding to the proximal end 16 of desired light guides 15 in light guide bundle 14 to an on-state and sets other pixels of the spatial light modulator to an off-state, thereby causing light from the light source 4 to be transmitted substantially only to the cores 26 of the light guides corresponding to the corresponding pixels. The controller can further select corresponding pixels that are set to an on-state such that light emanating from the distal end 18 of a first corresponding light guide 28 to a first area of target 22 does not substantially interfere with light emanating from the distal end 18 of a second corresponding light guide 28 to a second area of target 22, which means that light signals transmitted to the target are spaced apart such that the light signals ultimately detected or analyzed from the target 22 do not significantly impact each other.

In other words, several light guides 15 can be illuminated in parallel (referred to as illuminating a pattern of light guides). Preferably, the minimum center-to-center spacing of the light guides in the pattern is large enough such that the intensity distributions detected from the light guides do not significantly overlap. Parallel light guide-core illumination offers a speed advantage over single light guide-core illumination. Parallel light guide-core illumination can illuminate a pattern of light guide cores, detect and record the intensity data for each light guide, including confocal data if desired, then illuminate a different set of light guide cores using a different illumination pattern, detect and record the data, and so on until all desired light guide cores in the bundle (which can be all light guide cores present if desired) have been illuminated and the data recorded. The recorded data may then be processed to generate a image.

Additionally, spatial light modulator 8 can provide a dynamic illumination mask by varying the selected corresponding pixels that are set to an on-state can be varied over time. This provides an advantage because substantially all of the light guides 15 in the light guide bundle 14 can be illuminated without needing to move any of light source 4, spatial light modulator 8 or light guide bundle 14. Thus, the spatial light modulator 8 provides a mask that permits the selective illumination of individual light guide cores 26 (or patterns of light guide cores 26) in a light guide bundle 14.

For ease of understanding, in FIG. 1 light guide bundle 14 is depicted with only 7 cores 26 while spatial light modulator 8 has 141 pixels. A typical embodiment can employ a fiber bundle with hundreds to tens of thousands of fibers and a spatial light modulator with thousands to hundreds of thousands of pixels. Preferably, the spatial light modulator 8 provides at least 3 pixels for each core 26, further preferably 4, 5, 6 or more pixels At the distal end 18 of light guide bundle 14, photons from an illuminated light guide 15 are relayed to the target 22 by lens system 20. Target 22 is disposed in the image plane 24 of the sample, also known as an object plane. Typically, the distal end of the light guide bundle 14 is in a conjugate image plane of the sample. The target can be any desired structure or sample, including for example industrial materials such as computer chips in an assembly line, or industrial inspection and quality control, for example in the aerospace, aircraft or automobile industries. In a preferred embodiment, the target is an in vivo target, further preferably an internal in vivo target which means a target that is not found on the exterior of the body and thus is found within a body cavity, such as the digestive system, lungs, ears, or reproductive system, or accessed trans-cutaneously such as a knee, heart, brain or viscera. Such targets can be accessed using a large bore needle, a biopsy channel of a endoscope (in which case the viewing device of the present invention can actually be used inside another endoscope), a catheter, or an independent custom packaging configuration such as a stylus; all such items are included within the term endoscope for the purposes of the present invention to the extent that all permit imaging using the devices and methods of the present invention. In-focus structures located within target 22 at the object plane backscatter or otherwise emanate photons to the illuminating light guide 26, which light guide then functions simultaneously as the detection fiber. Out-of-focus structures, above or below the object plane or lateral to the illuminated target, backscatter or otherwise emanate photons to the adjacent light guides 30 surrounding the corresponding light guide 28.

A confocal image can be constructed by detecting, and analyzing if desired, the in-focus photons (those which are backscattered into the same light guide from which they were launched) and discarding or ignoring (e.g., failing to detect such light or detecting it then deleting it) the out-of-focus photons. Alternatively, light from adjacent light guides 30 can provide out-of-focus data and the programming can incorporate the out-of-focus data with the light emanating from the corresponding light guide 28 to provide an enhanced image.

For example, the out-of-focus data and the in-focus data can be fit to a 2D Gaussian distribution or according to other suitable fitting functions. See PCT/CA98/00993; PCT/US00/11548; U.S. provisional patent application No. 60/244,427, filed Oct. 30, 2000.

A confocal image comprising out-of-focus information can also be constructed as follows. A review of the background will be helpful.

The assumption in general microscopy is that a microscope is a linear shift-invariant (LSI) system. In deconvolution microscopy, the LSI assumption means that the PSF (point spread function) is assumed to be independent of position within the field of view (or use) of the microscope. Thus the image actually collected by the microscope (in either widefield or confocal modes) can be represented as a convolution of the actual physical fluorophore (or reflected light, transmitted light or other emanating light) distribution ($I_a(x,y,z)$) with the PSF $h(x,y,z)$ of the optical illumination and detection systems.

$$I_m(x, y, z) = \int \int \int I_a(x_i, y_i, z_i,) h(x - x_i, y - y_i, z - z_i) dx_i dy_i dz_i \quad 1$$

$$= \int \int \int I_a(x_i, y_i, z_i,) h_I(x - x_i, y - y_i, z - z_i) h_D(x - x_i, y - y_i, z - z_i) dx_i dy_i dz_i \quad 2$$

$h_I$=point spread function of illuminator optics
$h_D$=point spread function of detection optics For widefield illumination, $h_I(x,y,z)$ is essentially a constant over the volume measured. For a correctly set up conventional confocal microscopy, ignoring wavelength effects, $h_I(x,y,z) = h_D(x,y,z)$.

For a confocal microscope comprising a spatial light modulator in the illumination light path, for the spots of the target directly illuminated by the on-pixels of the spatial light modulator, the condition $h_I = h_D$ is generally true. For adjacent spots of the target, $h_D \approx h_I$. Assuming a LSI system and ignoring the wavelengths effects, $$h_D(x,y,z) = h_I(x-x_i, y-y_i, z-z_i) \quad 3$$

Also, locations in the x-y plane of the sample, $z_i = 0$. Thus, equation 3 can be reduced to:

$$h_D(x,y,z) = h_I(x-x_i, y-y_i, z) \quad 4$$

Since a plurality of spots can be detected for each spot illuminated by the on-pixels of the spatial light modulator, most of the image consists of out-of-focus pixels for which $h_D \not\approx h_I$. Thus the following equation generally applies for a confocal system as described herein:

$\xi, \beta = 0$ in-focus $$I_m(x,y,z,\xi,\beta) = \iiint I_a(x_i,y_i,z_i) h_I(x-x_i, y-y_i, z-z_i) h_D(x-x_i, y-y_i, z-z_i, \xi, \beta) dx_i dy_i dz_i$$

$\xi, \beta \approx 0$ out-of-focus

An additional 2 dimensions (co-linear with x and y), which represent the out-of-focus light collected from the sample and generated by the confocal illuminator associated with the confocal spot, is associated with each set of x,y,z confocally illuminated locations. Generally for widely spaced spot intervals, such as a 10×10 spot pattern, $\xi$ and $\beta$ run from −5 to +5 in units of the projected DMD pixels in the sample plane. The spacing of the spots and the range of $\xi$ and $\beta$ uncontaminated by adjacent spot out-of-focus information can be dependent on the thickness of the sample being measured.

Generally, deconvolution methods such as iterative deconvolution methods compare the results of the deconvolution with the measured image by convolving the point spread function with the deconvolved image to generate an image.

$I_m(x,y,z)$ should be the convolution of $I_{a\ guess}(x,y,z)$ with the PSF.

$I_{a\ guess}(x,y,z)$ convolved with PSF gives $I_{m\ guess}(x,y,z)$.

Thus, measure the difference between $I_{m\ guess}(x,y,z)$ and $I_m(x,y,z)$, update $I_{a\ guess}(x,y,z)$ and iterate until a desired performance measure condition is met.

According to the present invention, to find $I_a(x,y,z)$, one may $I_{m\ guess}(x,y,z)$ with $I_m(x,y,z)$ and also $I_{m\ guess}(x,y,z,\xi,\beta)$ with $I_m(x,y,z,\xi,\beta)$. This can enhance the result, in pan, because $I_m(x,y,z,\xi,\beta)$ for $\xi,\beta \approx 0$ is highly dependent on the PSF and is likely not mixed with the confocal information of $I_m(x,y,z,0,0)$. Thus, the present invention comprises methods and devices that take advantage of the additional measurements that are dependent upon the spatial arrangement of $I_a(x,y,z)$. In addition these methods and devices use substantially all the photons collected, from the target not just the photons emanating directly into the corresponding light guide so the signal to noise is improved.

In-focus confocal information and out-of-focus information can be obtained in both the x-y directions and in the z-direction, for example if the camera dr spatial light modulator is moved along the optical (z) axis or by providing multiple cameras at different primary focal plane positions immediately above and below the focal plane of the illumination focal plane.

An alternative embodiment provides as follows. In conventional confocal microscopy the sample is illuminated by a point source which is broadened by the illumination PSF into a distributed light source pattern within the sample. The resulting returned light (such as fluorescence light) emanating from the sample has a similar detection sensitivity pattern (PSF). The differences between the two patterns or distributions, for example for fluorescent light can be due to the Stokes shift in the emitted light because fluorescent light is of a longer wavelength than the excitation light. In conventional confocal imaging these two patterns are multiplied together to provide a confocal PSF function. While most of the information detected is at the center peak, the distribution extends in both the x-y and z directions quite significantly.

The interaction of the PSF of the illumination with the PSF for the pixels of the detector and the optical system transmitting the emanating light to the detector that are detecting the out-of-focus light is complex. Around the central peak of the conventional confocal distribution, translated (x-z) detection spots detect information from the front and sides of the conventional central peak as well as from the cones in front (small z's) and behind (large z's) the conventional peak. Subtracting the out-of-focus data from the in-focus data generates results wherein the width and length of the central peak is much smaller than the conventional confocal PSF. In alternative embodiments, only the lateral out-of-focus data is used. In other words, the PSF has been narrowed, which means that the resolution has been enhanced. Also, the information collected from the cones before and after (smaller and longer z values) is much less than in the conventional confocal PSF. Another indication of the improvement is the FWHM of the modified PSF, which is significantly less than the FWHM of the conventional confocal PSF. This indicates higher spatial resolving power for the methods and systems of the present invention.

One advantage of using the out-of-focus information surrounding illuminated spots is that if the PSF changes from location to location in the field of view (system is not LSI), the methods and systems of the present invention have lower sensitivity to local changes in the PSF. Another advantage is that the post-processing required to make use of the out-of-focus information can be simplified in some embodiments because it may need only a convolution of a kernel with the raw images of the illumination spot patterns, and the methods and systems can be easily re-configurable to optimize desired aspects of the PSF. For example, if a very narrow PSF in the x direction is required but the y and z directions are not as critical, the out-of-focus information can be used to maximize the x axis resolution at the expense of the y and z axis resolution. This can be done dynamically or after the images have been acquired.

In transmission microscopy, it is difficult to do confocal microscopy because the light passes through the entire sample to be detected. Thus, localized z measures of the absorbing material is difficult to do in thick samples. However, using the out-of-focus information after appropriate logarithmic transformation of the raw illumination spot (column) images, create modified PSF's which have a localized z information content. This provides a modified PSF and, if desired, z slices.

In further embodiments, the methods and apparatus are used for confocal microscopy wherein the optical set-up of the microscope is not optimized, which means that the optical elements of the microscope are not properly aligned or placed such that the actual imaging achieves an image quality less than about 95% of the theoretically achievable resolution for the given system or where the target causes significant optical artifacts such as spherical aberrations due to the preparation method (such as fixing, mounting, staining, labeling).

As with other features of the present invention, these embodiments and aspects can be implemented using a controller and suitable computer-implemented programming.

Out-of-focus data can imply properties about a target, such as reduced or increased scattering coefficients and absorption coefficients.

Figure 2:
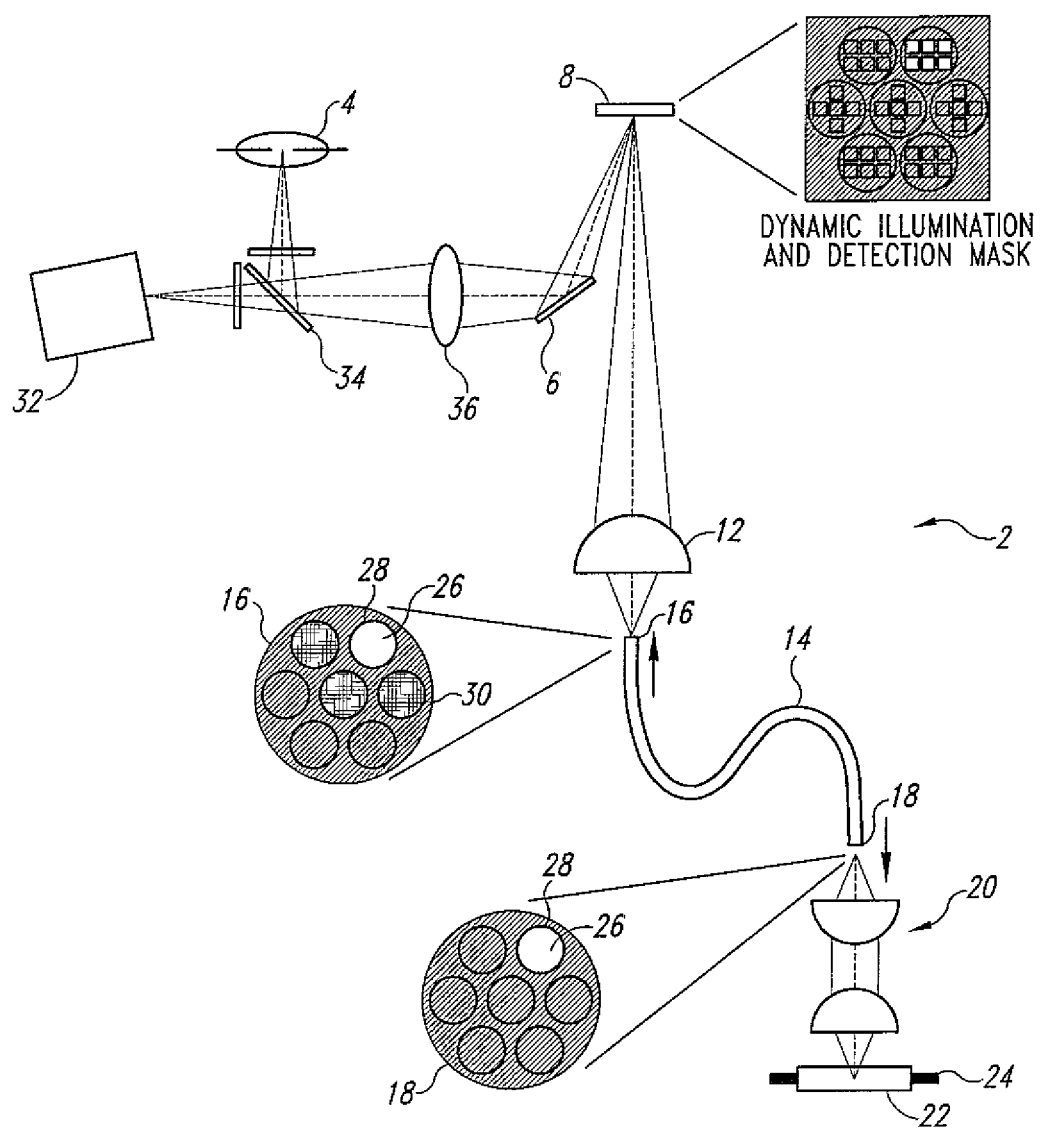
FIG. 2 provides a schematic view with expanded schematic views of a double-pass viewing device comprising a spatial light modulator and a light guide bundle.

FIG. 2 depicts a schematic view with expanded schematic views of a double-pass embodiment wherein spatial light modulator 8 is simultaneously employed as an illumination and detection mask; in the embodiment depicted the spatial light modulator 8 is a dynamic mask. The embodiment depicted comprises substantially the same components, plus a filter block assembly 34 and a relay lens 36 disposed in the illumination/detection light path. The spatial light modulator 8 acts as a mask that permits the selective illumination of and detection of light from the cores 26 of corresponding light guides 28 (or patterns or groups of corresponding light guides 28) in light guide bundle 14. The embodiment is referred to as "double-pass" because a single spatial light modulator 8 is present in both the illumination (first pass) and detection (second pass) light paths.

The double-pass embodiment can provide additional functionality compared to the single-pass embodiment. In addition to illuminating a core 26 of a corresponding light guide 28 (or a (i.e., group) of such cores), the double-pass embodiment is able to accept light emitted by the core 26 of that same corresponding light guide 28 while rejecting (or masking) that light that is emitted from a region around the light guide(s). This allows the spatial light modulator 8 and the cores 26 of corresponding light guides 28 of the light guide bundle, working in concert, to act as both the illumination and detection pinholes of a confocal system. In a single-pass embodiment, out-of-focus information is typically rejected using computer-implemented programming, such as a software algorithm, that masks or removes such information from each image acquired by the detector. The double-pass embodiment shifts the burden of rejecting out-of-focus information from software (which is relatively slow and resource intensive) to hardware (which is relatively fast and uses fewer-resources). For various embodiments, confocal images can be produced by summing or integrating the set of intensity distributions returned by the light guide bundle, which set can be filtered by the spatial light modulator in the double-pass embodiment.

Figure 3:
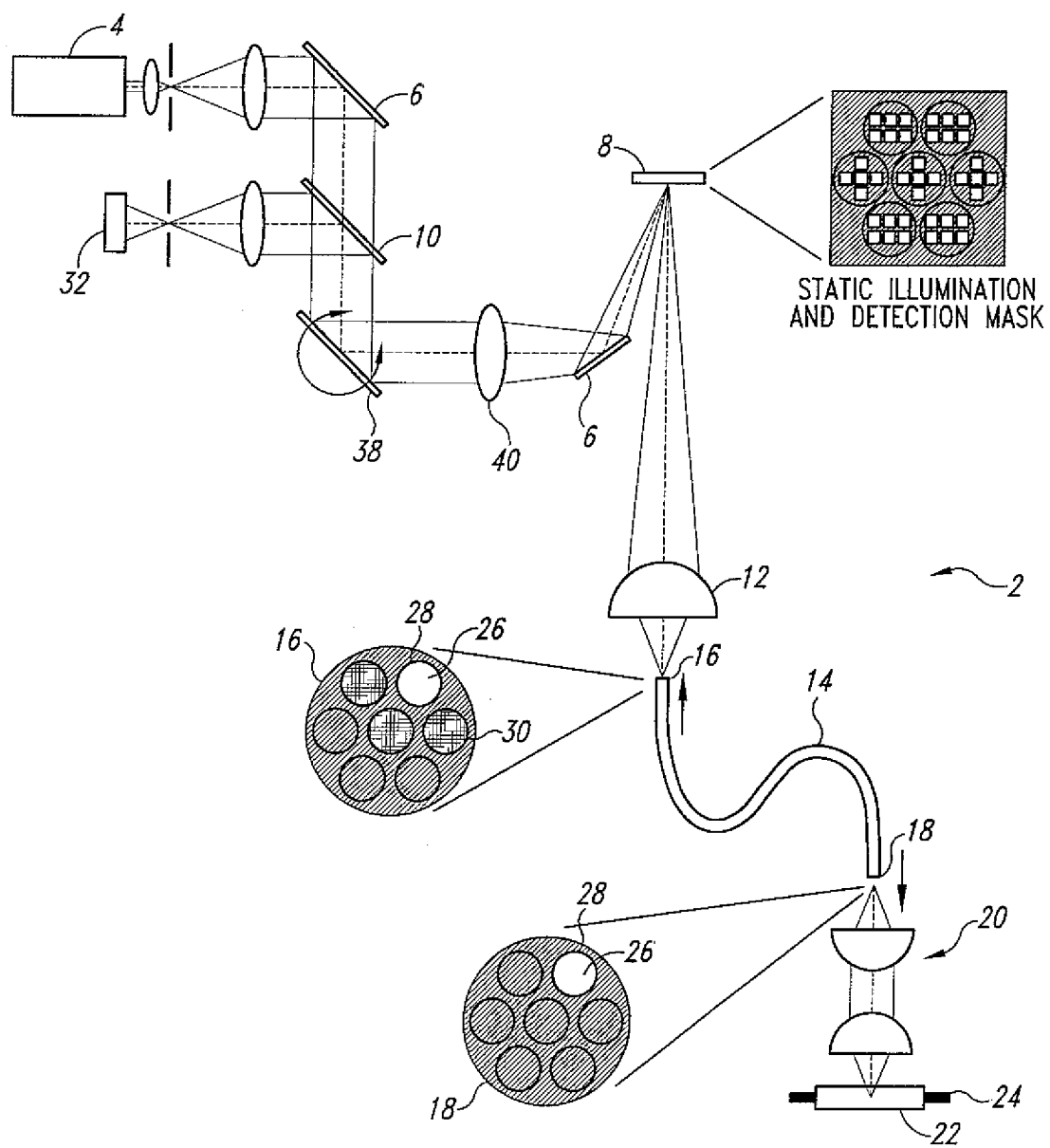
FIG. 3 provides a schematic view with expanded schematic views of a double-pass viewing device comprising a spatial light modulator and a light guide bundle wherein the illumination light is scanned across the spatial light modulator.

FIG. 3 provides a schematic view with expanded schematic views of a double-pass viewing system wherein the illumination light is scanned across spatial light modulator 8 by a galvanometer or x-y scan mirror 38 or similar scanning device; scanning can also apply to single pass embodiments. In FIG. 3, the spatial light modulator 8 is employed as a static illumination and detection mask to illuminate the cores 26 of corresponding light guides 18 of the light guide bundle, and then to detect light emitted only from the same corresponding light guides 28. The spatial light modulator-based static mask depicted in FIG. 3 provides advantages over a simple pinhole array. For example, a typical light guide bundle may use an approximately hexagonal packing structure. This causes the center-to-center spacing of the light guides to vary and the shape of each cote can be irregular. Consequently, it is difficult to construct a spatially variant hexagonal pinhole array using standard laser drilling techniques, for example because the pinhole array could need to be realigned fairly frequently and could need to be specific for each bundle Constructing such a static mask as described herein, using a spatial light modulator, is relatively easy. This embodiment is particularly useful for traditional confocal microscopes such as a confocal laser-scanning microscope (CLSM), a tandem scanning microscope (TSM) or a programmable-array microscope (PAM), although it can also be used with other viewing systems.

Many of the embodiments discussed herein involve mapping the pixels of a spatial light modulator, cores of corresponding light guides, additional light guides and/or a detector, for example when the detector is pixelated detector The present invention additionally provides methods and apparatus for such mapping, both as a part of other aspects of the present invention and for the mapping itself. Mapping can also be referred to as registration, particularly when referring to the association of the pixels of a spatial light modulator or light guides in a light guide bundle to the pixels of a pixelated detector. In one embodiment, a pixelated detector such as a CCD camera "takes pictures" of the light guide bundle and the spatial light modulator. The "pictures" indicate the spatial arrangement of the pixels (i.e., the optical switches) of the spatial light modulator and cores of light guides relative to the pixels of the pixelated detector The pixels of the spatial light modulator and the pixelated detector are then registered with the cores of the corresponding light guides.

Figure 4:
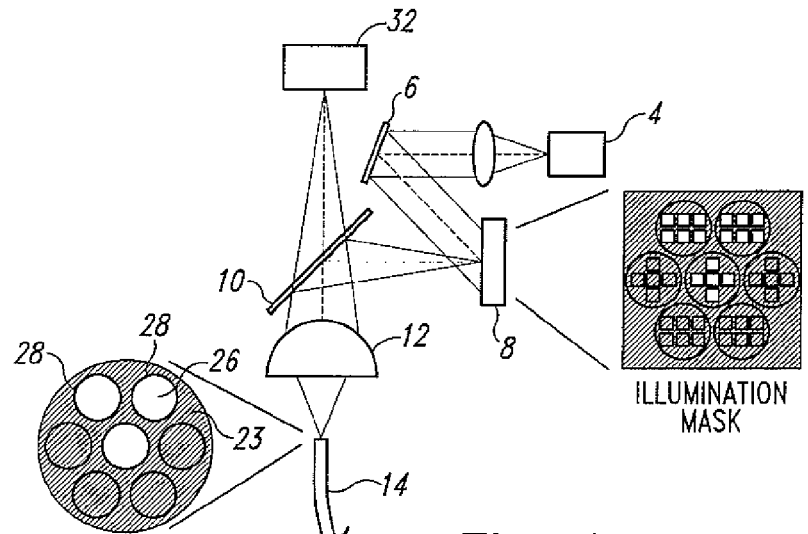
FIG. 4 provides a schematic view with an expanded schematic view of a system set up substantially the same as the systems in FIGS. 1 to 3, from the light source to the proximal end of the light guide bundle, for mapping pixels and light guides.

FIG. 4 depicts a system set up substantially the same as the systems in FIGS. 1 to 3, from the light source to the proximal end of the light guide bundle. In order to map the pixels of the spatial light modulator 8 to the pixelated detector 32, replace the light guide bundle 14 in FIG. 4 with a reflecting surface such as a plane mirror (not shown). Next write a registration pattern on the spatial light modulator, typically via computer-implemented programming in a controller (not shown), then acquire an image of the registration pattern using the pixelated detector. This first registration image maps the pixels of the spatial light modulator to the pixels of the pixelated detector. A second registration image can then be obtained by replacing the plane mirror with the light guide bundle 14 as shown in FIG. 4, and illuminating the light guide bundle 14 at its distal end. This provides a corresponding image of the light guide bundle 14 on the pixelated detector This second registration image maps the cores 26 of light guides 15 in the light guide bundle 14 to the pixels of the pixelated detector. The two registration images can then be combined to map the spatial light modulator to the light guide bundle. In particular, since the first registration image maps the pixels of the spatial light modulator to the pixels of the pixelated detector, and the second registration image maps cores of light guides to the pixels of the pixelated detector, the two can be compared to map the pixels of the spatial light modulator to the cores of the light guides.

Figure 5:
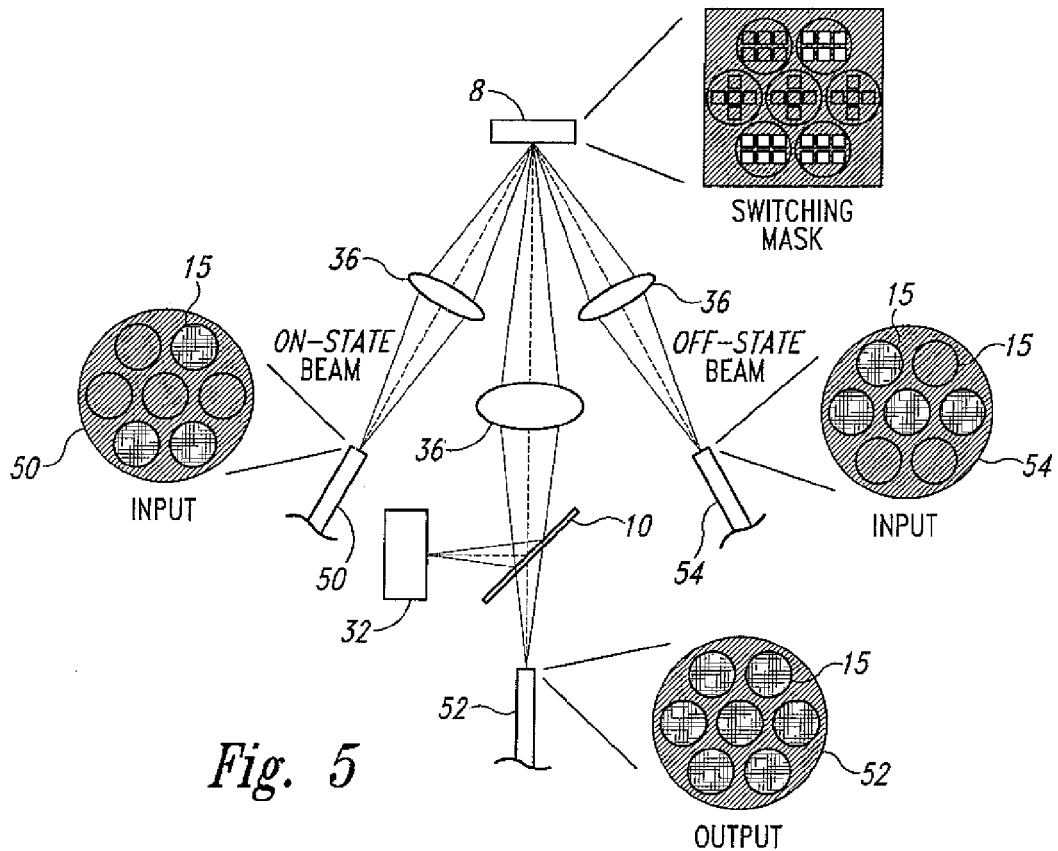
FIG. 5 provides a schematic view with expanded schematic views of a system for mapping pixels of a spatial light modulator and light guides.

FIG. 5 provides a schematic view with expanded schematic views of a system far mapping pixels of a spatial light modulator 8 to one or more light guides 15 and for light guide to light guide mapping. In this embodiment, a plurality of registration images, preferably at least two or three, are combined to map the cores of light guides in one light guide bundle to at least one other light guide bundle, preferably two other light guide bundles as in FIG. 5. In FIG. 5, the spatial light modulator as described is a digital micromirror device. However, other spatial light modulators can also be suitable.

Mirrors (pixels) in a digital micromirror device can be flat, tilted +10° (which can represent an on-state), or tilted −10° (which can represent an off-state). Thus, when the mirrors in the digital micromirror device 8 are flat, or parked, the pixelated detector can acquire an image of second light guide bundle 52 (which can be an output or light emitting bundle). When the mirrors in the digital micromirror device 8 are tilted at +10°, the pixelated detector can acquire an image of first light guide bundle 50 (which can be an input or light accepting bundle). Similarly, when the mirrors in the digital micromirror device 8 are tilted at −10°, the pixelated detector can acquire an image of third light guide bundle 54 (which can be an input or light accepting bundle). This provides three maps or registration images. Fiber-to-mirror-to-fiber mapping can be determined for each optical pathway (e.g., second light guide bundle 52-to-first light guide bundle 50-to-third light guide bundle 54) by combining the three registration images.

In one embodiment, the mapping can proceed as follows:

1. Illuminate the cores of the light guides of second light guide bundle 52. Park the mirrors in digital micromirror device 8 and acquire an image of the fiber cores using the pixelated detector.

2. Illuminate the cores of the light guides of first light guide bundle 50. Switch the mirrors in digital micromirror device 8 into their on-state of +10° and acquire a registration image using the pixelated detector 3. Similarly, illuminate the cores of the light guides of third light guide bundle 54. Switch the mirrors in digital micromirror device 8 into their off-state of −10°and acquire an image using the pixelated detector.

4. Combine the registration images to establish light guide-to-spatial light modulator-to-light guide mapping, as well as, for example, light guide-to-light guide-to-light guide mapping.

Thus, the present invention provides methods and systems relating to mapping, including mapping one light guide to another, one spatial light modulator to another, a light guide or a spatial light modulator to a target or detector, and combinations thereof. Generally, a registration pattern of one light guide, spatial light modulator or other desired item is obtained, typically using a pixelated detector or 1 other detector able to distinguish different pixels of light impinging on the detector, then obtaining a second registration pattern of a second one light guide, spatial light modulator or other desired item is obtained, then the two are compared. In some embodiments, the method further comprises moving one of the mapped items relative to another such that they are more closely aligned, or adjusting the pixels on an intervening spatial light modulator to effectively provide enhanced alignment as well as devices to perform such adjustments of the mapped items or pixels.

Turning to another feature of the present invention, one of its advantages is that it can also be used with a non-coherent light guide bundle FIG. 6 provides a schematic view of a coherent and a non-coherent light guide bundle. In the coherent bundle in panel (a), the location of individual light guides 15 at the proximal end of light guide bundle 14 is substantially the same as at the distal end; in the non-coherent bundle in panel (b), the location of individual light guides 15 at the proximal end of light guide bundle 14 varies from then relative location at the distal end. Thus, in the coherent bundle shown in panel (a), the light guide bundle transmits a coherent image from one end of the bundle to the other. In the non-coherent bundle shown in panel (b), the illuminated fiber's are arranged such they are grouped together at the illumination end but uniformly distributed over the entire bundle at the emission end. The center-to-center spacing of the illuminated fibers at the distal, i.e., emission, end is preferably large enough that the detected intensity distributions do not substantially overlap. Such a non-coherent bundle allows a light guide bundle scanned with a conventional spot of light (e.g., a spot generated from a galvanometer or similar scanning device) to produce a set of suitably-spaced parallel illumination spots that substantially avoid overlap in their detected intensity distributions even when on-pixels of the illumination mask are not adequately spaced apart. The ultimate image can be constructed because the data taken in by the pixels of the pixelated detector can be reconstructed using the map created using the mapping approaches described herein. Thus, coherent images may be obtained using less expensive non-coherent light guide bundles Turning to some general comments about the systems and focus, the distal end of the light guide bundle may be mounted in conjunction with a lens system (such as a GRIN lens, a small standard lens or lens set, a shaped GRIN lens, a diffractive lens or any these in combination) to de-magnify the projected illumination pattern into the tissue and to magnify the backscattered, fluorescence or other emanating light to be detected.

It can be desirable to move the confocal image plane along the optical axis of the light guide bundle lens system to interrogate different tissue depths. This can be performed, for example, by mounting a piezo-electric element or other length-extending device or material, which can be in the shape of a cylinder or other desired configuration, at the distal end of the light guide bundle. Changing the voltage on the piezo-electric element changes its length, so the distance between the light guide bundle and any lens(es) located distal to the distal end would also change. Thus, the position of the sample focal plane or object plane in the tissue would change. The piezo-electric element could be placed, for example, along the distal end of the light guide or light guide bundle, between the light guide bundle and the lens or between the lens(es) and the end of the viewing device (such as an endoscope), such as a viewing window Additionally, it can be desirable to reduce the backscatter from index-of-refraction mismatches at either end of light guide bundle, which can reduce the image contrast and reduce the amount of light transmitted into or received from the target. Thus, in one embodiment an optical coupling fluid with an index of refraction similar to those of the cores of light guides in the bundle and the lens(es) couples the light from the light guide into the lens and vice-versa. This index-matching may be used at both the proximal and distal ends of the light guide bundle.

The present invention can also be useful in conventional microscopy and endoscopy. For example, a conventional endoscope has a field-of-view appropriate for the visualization of internal organs. A microendoscope, however, has a relatively small field-of-view (typically 100-400 µm in order to image tissue at the cellular level. A conventional endoscope employs separate light guide bundles for illumination and detection in order to achieve acceptable contrast. A microendoscope typically employs a single light guide bundle for illumination and detection. The method and devices described herein, such as those relating to pixel-to-core illumination and detection, and light guide-to-light guide mapping, can be used with such conventional devices to achieve acceptable or improved contrast. A conventional endoscope can therefore be constructed that requires only a single light guide or light guide bundle for illumination and detection. This allows such a device to have a smaller outside diameter and thus to access parts of the body that are currently difficult to reach.

The present invention can also be used for in vivo confocal imaging of tissue optical properties or other desired purposes using an optical imaging system, such as in a rigid endoscope. For example, a second spatial light modulator can be employed in a conjugate image plane of an aperture diaphragm of the objective lens of a traditional microscope or other viewing system to control the angles of illumination. Since the light initially entering the tissue will propagate in its initial direction for at least approximately one mean-free path length (a tissue or target dependent parameter), images generated with different illumination angles can be combined to glean information about tissue at different depths.

In one embodiment, focusing on the top of the tissue using different angles of illumination, i e −45°, 0° and +45° in the x-z plane, −45° and +45° in the y-z plane, and −45° and +45° in each of the two x-y diagonal planes, generates a surface enhancing image, Q= 0° image—(all the 45° images/# of 45° images) for each illumination spot pattern. A complete confocal image is the sum of all the Q images. The inverse procedure gives an image which shows more information from deeper within the tissue.

Thus, the present invention provides methods and systems relating to the optical interrogation of a target such as tissue, including human tissue, as well as non-living targets such as computer components and devices suitable for use in other industrial settings comprising illumination and detection using a single, large-bore light guide capable of transmitting an angle of light, either illumination light or detection light, or both. This aspect can generate enhanced images of the target at different depths. In one embodiment, the methods comprise focusing on a desired level within the target using different angles of illumination to generate an enhanced image where a confocal image can be generated by summing substantially all images from the given depth.

The present invention also provides methods of making and using the devices and systems described herein, as well as methods that can be applied to other devices and systems. For example, viewing systems can be made by optically connecting a spatial light modulator to the proximal end of a light guide bundle in a same conjugate image plane as the proximal end such that the spatial light modulator controls the location of light impinging on the proximal end. The viewing system can be a confocal microscopy endoscope and the light guide bundle preferably comprises at least 100 light guides. In other embodiments, the viewing system can use a single light guide. The spatial light modulator can either be located in a same image plane as the proximal end, in which case the spatial light modulator can control the location of the illumination light on the light guide(s), or the spatial light modulator can be located in an image plane that permits the spatial light modulator to control the angle of the illumination light as it impinges upon the optical imaging system. This and various other methods and features of the present invention, can be implemented using a controller and computer-implemented programming. In one embodiment, the programming sets to an on-state pixels of the spatial light modulator corresponding to cores of corresponding light guides in the light guide bundle to provide on-pixels and sets to an off-state pixels corresponding to inter-core areas of the light guide bundle to provide off-pixels.

The system can further comprise an optically connected light source to provides light to the light guide bundle and a pixelated detector that receives light emanating from the proximal end of the light guide bundle. The system, typically via the detector, can be combined with the controller with computer-implemented programming to distinguish between light emanating from the light guides corresponding to on-pixels of the spatial light modulator and light emanating from other light guides. The system can be either a single-pass viewing system or a double-pass viewing system, and the spatial light modulator can act as a dynamic illumination or detection mask, or a scanner can be provided that controls the location of light transmitted to the spatial light modulator and on to the proximal end of the light guide bundle.

A target can be illuminated by transmitting light from a light source to a proximal end of a light guide bundle via a spatial light modulator wherein the spatial light modulator transmits the light substantially only to cores of light guides in the light guide bundle; transmitting the light from the proximal end of the light guide bundle to a distal end of the light guide bundle and emitting the light from the distal end of the light guide bundle; and, illuminating the target with the light emitted from the distal end of the light guide bundle. The methods can comprise scanning a light beam across the spatial light modulator and simultaneously setting at least one pixel of the spatial light modulator that corresponds to a core of one of the light guides to an on-state to provide at least one on-pixel and setting other pixels of the spatial light modulator to an off-state, whereby the light beam is transmitted substantially only to the core of the light guide when the light beam contacts the on-pixel and the light beam is not transmitted to inter-core areas of the light guide bundle or to light guides adjacent to the light guide. In one embodiment, the methods comprise illuminating an internal in vivo target.

An image of a target can be obtained, for example, by transmitting light from a light source via a spatial light modulator to a light guide bundle, then emitting the light from a distal end of the light guide bundle to illuminate the target and thereby cause light to emanate from the target to provide emanating light; collecting the emanating light that contacts the distal end of the light guide bundle; and transmitting the emanating light via the light guide bundle to a detector to provide an image of the target at the detector. The image can be observed, for example, by either an eyepiece ocular or a pixelated detector, and the image can be a widefield or a confocal image, or other desirable image. Additionally, the image can be an internal image of an in vivo target and can be obtained through an endoscope.

EXAMPLE

A system according to FIG. 1 was constructed to demonstrate confocal imaging through a fiber bundle. A digital micromirror device (DMD) from Texas Instruments (Dallas, Tex) was employed as the SLM because of its high contrast high pixel count, and fast temporal response. The DMD micromirrors had a center-to-center spacing of 17 μm and a mechanical switching time of 15 μs. L. J. Hornbeck, Proc SPIE 3013, 27 (1997). A 640×480 resolution DMD with a full on-off contrast ratio of 255:1 was employed in this work; higher resolution (1280×1024) and increased contrast (370:1) devices are now available.

A Sumitomo IGN-08/30 image guide (30,000 fibers, 2 μm fiber diameter, 3 μm center-to-center spacing, 0.35 NA) was positioned in the object plane of a conventional microscope configured for 1 reflected light epi-illumination. The DMD was positioned in the illumination path of the microscope such that it was conjugate to the object plane. The contrast of the DMD was maximized because the image-side NA of a microscope objective was generally much less than the maximum value of 0 18 suggested by Hornbeck, *Proc. SPIE:* 3013, 27 (1997), for optimum contrast. A CCD camera was positioned in the primary image plane of the microscope. The DMD was uniformly illuminated with blue (400-500 nm) filtered light from an EFOS (Mississauga, ON) X-Cite mercury arc lamp. The objective lens L1 was a Nikon 2.0× Plan Apochromat.

The DMD mirrors and CCD pixels were registered with the fibers of the image bundle in a two-step calibration procedure. First, a plane mirror was positioned in the object plane of the microscope (the proximal end of the image bundle as shown in FIG. 1 was temporarily replaced with a plane mirror). A registration pattern was written to the DMD and an image was acquired using the CCD camera. This first registration image was used to map DMD mirrors to CCD pixels. The image bundle was then placed into the object plane of the microscope and illuminated at its distal end. An image was acquired of the fiber bundle. This second registration image was used to map fibers in the bundle to CCD pixels. Taken together, the two registration images were employed to map DMD mirrors to individual fibers. In the experimental results reported here, there were, on average, 6 mirrors mapped to each fiber in the bundle. The mapping of mirrors to fibers, for 7 typical fibers, was illustrated in the illumination mask of FIG. 1.

A fiber in the image bundle was illuminated by activating those mirrors on the DMD which corresponded to that fiber. At the distal end of the fiber, photons from an illuminated fiber were relayed into the specimen by a lens system. This double-objective lens system was composed of two Nikon Plan Achromat lenses (20× 0.75-NA and 60× 1.40-NA oil immersion) placed back-to-back around a field lens to provide 3× magnification. In-focus structures located within the specimen at the object plane backscattered photons to the illuminating fiber. Out-of-focus structures, above or below the object plane, backscattered photons to the set of fibers adjacent to the illuminating fiber. A confocal image was constructed by saving the in-focus photons (those which were backscattered into the same fiber from which they were launched) and discarding the out-of-focus photons.

The optical efficiency of the illumination path was determined by measuring the optical power incident on the proximal end of the fiber bundle and that emitted from its distal end. When only those mirrors assigned to individual fiber cores where activated, the optical efficiency was 30%. This efficiency includes losses due to fiber attenuation, Fresnel reflections at each end of the fiber bundle, and any fiber-to-mirror misalignment. When the entire fiber bundle was illuminated by activating all of the mirrors, the optical efficiency dropped to 19%. The efficiency dropped under full illumination because light incident on the inactive material between fiber cores, or inter-core material, was not efficiently transmitted by the fiber bundle. This wasted light was either backscattered, reducing the contrast of the system, or coupled into the cladding and then either absorbed by the fiber jacket or re-coupled into a nearby fiber.

Figure 7:
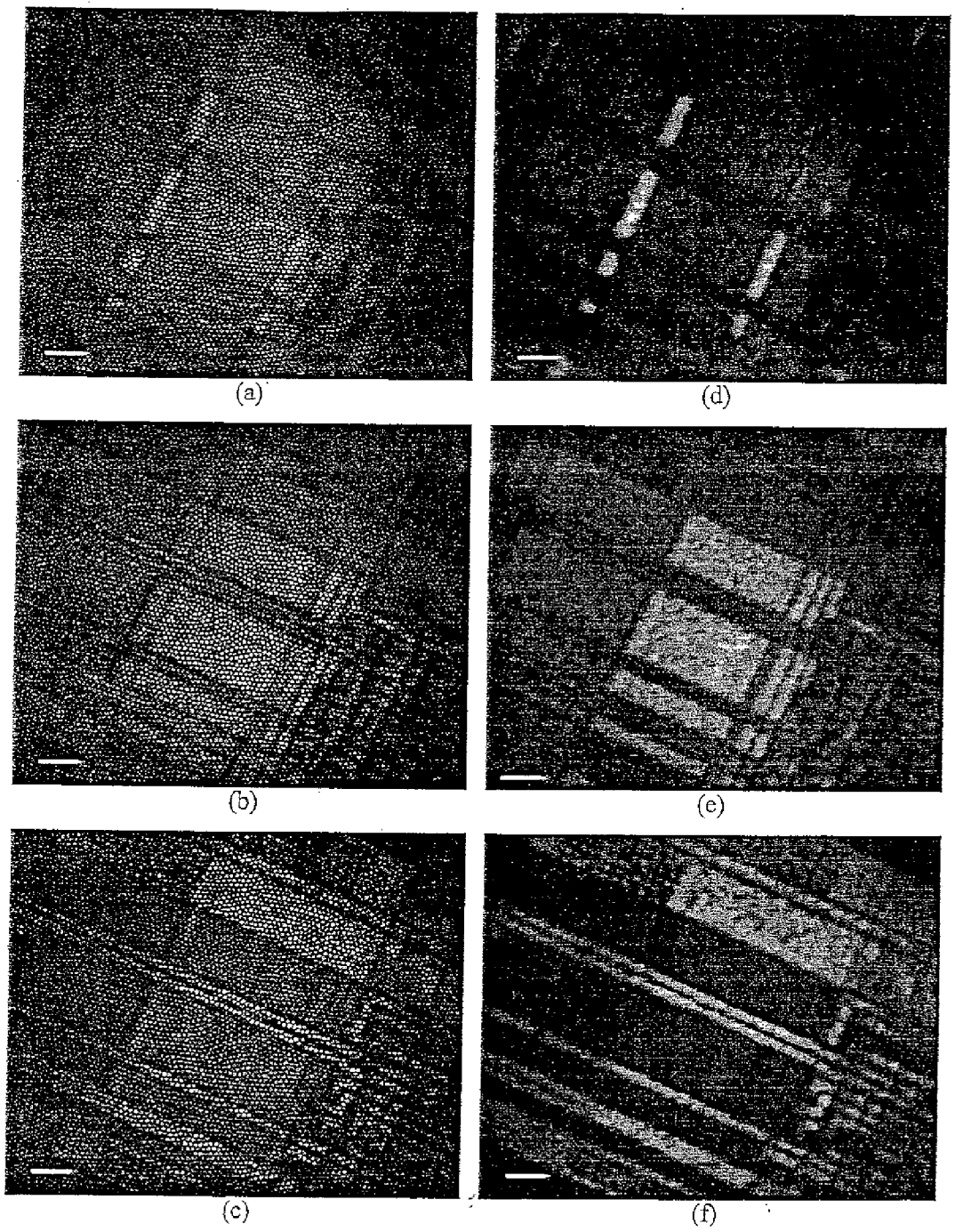
FIG. 7 provides photomicrographs of an microprocessor comprising widefield images ((a) to (c)) taken using a widefield microscope and confocal images ((d) to (e)) taken using a confocal microscope according to the present invention.

Images acquired with the system were illustrated in FIG. 7. Parts (a) through (c) show conventional (widefield) images of an Intel 80486 microprocessor imaged at three different focal planes. The corresponding confocal images are shown in parts (d) through (f). The axial distance between the focus levels was 2 μm and the scale bar on each image was 10 μm in length. In-focus features appear in both sets of images; out-of-focus features appear in only the widefield images and were generally absent in the confocal images. The fiber structure was clearly visible in the three widefield images. In the confocal case, the fiber structure was not as visible because the total in-focus intensity integrated over the core area of each fiber was written to the final image as a smooth Gaussian spot. An average gray level of 25 was observed at the fiber cores when the signal reflected from the target was blocked. In-focus structures which caused the fibers to saturate the 8-bit detector therefore had a contrast of 10:1. Much higher contrasts will be obtained when the fiber bundle is properly coupled to the objective lenses using an index matching fluid.

The axial response of the system was characterized by translating a plane mirror through focus. The response when a single fiber at the center of the field was illuminated was shown in FIG. 8. The FWHM was 1.6 μm. In this confocal system, each fiber in the imaging bundle provides the function of an illumination and detection pinhole. The effective diameter of the confocal pinhole was therefore determined by the average diameter of the fibers. The normalized diameter of the pinhole, projected through the lens system into object space, was $v_p = kd_0 \, NA/M$, where $k=2\pi/\lambda$, $d_0$ was the fiber diameter, and M was the magnification. Here we assume that the diameter of the fiber core was equal to the FWHM of its intensity distribution, $d_0 \approx d_{FWHM} = 2.5$ μm. The NA of the lens system was $3 \cdot 0.35 = 1.05$ (the effective NA of the lens system was limited by the NA of the imaging bundle projected through the lens). At a wavelength of $\lambda = 450$ nm, $v_p = 6.11$, and consequently, the theoretical variation of on-axis intensity with defocus was not described well by the simple sinc(z) paraxial formula. A theoretical FWHM of 1.07 μm was calculated for this confocal system following the method of Wilson and Carlini, *Opt. Lett.*:12, 227 (1987). The difference in the theoretical and observed FWHMs was due mainly to the non-uniform photon density across the fiber pinhole. The theoretical calculation assumes uniform illumination and detection pinhole functions which was not true for a fiber illumination pinhole with a Gaussian-like intensity distribution.

Employing an SLM to selectively illuminate individual fibers rather than simply scanning a spot over the fiber bundle can improve the optical sectioning ability of a fiber-optic confocal microscope. In a conventional scanned-spot system, as the spot passes over the inter-fiber (inter-core) region of the light guide bundle, up to three fibers may be illuminated simultaneously (assuming hexagonal fiber packing). Because the spot intensity can be redistributed as the light propagates down each of the three fibers, the effective pinhole diameter might be increased by a factor of up to two or more. The increase in pinhole diameter can reduce the optical sectioning capability of the system. When light guides were illuminated individually by employing an SLM, substantially only one fiber (or discrete fibers) was illuminated at a time and the effective pinhole diameter was typically equal to the diameter of the fiber. This provides a smaller FWHM and enhanced optical sectioning. In addition, illuminating individual fibers with an SLM also leads to higher contrast and improved optical efficiency because all photons incident on the fiber bundle were coupled into a specific fiber core and very few photons were backscattered from the interstitial material between fibers.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A viewing system comprising a spatial light modulator and a light guide bundle having a proximal end and a distal end, wherein spatial light modulator is optically connected to the proximal end of the light guide bundle in a same conjugate image plane as the proximal end such that the spatial light modulator controls the location of light impinging on the proximal end, wherein the spatial light modulator is operably connected to a controller comprising computer-implemented programming configured to set to an on-state pixels of the spatial light modulator corresponding to cores of corresponding light guides in the light guide bundle to provide on-pixels and configured to set to an off-state pixels corresponding to inter-core areas of the light guide bundle to provide off-pixels, wherein the viewing system further comprises a pixelated detector optically connected to receive light emanating from the proximal end of the light guide bundle and the controller further comprises computer-implemented programming that distinguishes between light emanating from the light guides corresponding to on-pixels of the spatial light modulator and light emanating from other light guides, and wherein the controller further comprises computer-implemented programming that detects light emanating from the other light guides to provide out-of-focus data and the programming incorporates the out-of-focus data with the light emanating from the light guides corresponding to the on-pixels to provide an enhanced image.

2. The viewing system of claim 1 wherein the controller fits the out-of-focus data and the light emanating from the light guides corresponding to the on-pixels using a 2D Gaussian distribution.

3. A viewing system comprising a spatial light modulator and a light guide bundle having a proximal end and a distal end, wherein spatial light modulator is optically connected to the proximal end of the light guide bundle in a same conjugate image plane as the proximal end such that the spatial light modulator controls the location of light impinging on the proximal end, wherein the spatial light modulator is operably connected to a controller comprising computer-implemented programming configured to set to an on-state pixels of the spatial light modulator corresponding to cores of corresponding light guides in the light guide bundle to provide on-pixels and configured to set to an off-state pixels corresponding to inter-core areas of the light guide bundle to provide off-pixels, wherein the viewing system further comprises a pixelated detector optically connected to receive light emanating from the proximal end of the light guide bundle and the controller further comprises computer-implemented programming that distinguishes between light emanating from the light guides corresponding to on-pixels of the spatial light modulator and light emanating from other light guides, wherein the controller further comprises computer-implemented programming that detects light emanating from the other light guides to provide out-of-focus data and the programming incorporates the out-of-focus data with the light emanating from the light guides corresponding to the on-pixels to provide an enhanced image, and wherein the controller further comprises computer-implemented programming that maps pixels of the spatial light modulator to corresponding cores of corresponding light guides in the light guide bundle to provide a map comprising corresponding pixels and non-corresponding pixels.

4. The viewing system of claim 3 wherein the viewing system further comprises a scanner that controls the location of light transmitted to the spatial light modulator and on to the proximal end of the light guide bundle, and the controller further comprises computer-implemented programming that directs the scanner to scan the spatial light modulator and simultaneously sets at least one of the corresponding pixels to an on-state and sets other pixels of the spatial light modulator to an off-state, thereby causing light from the light source to be transmitted substantially only to the cores of corresponding light guides.

5. A flexible endoscope system providing confocal microscopy of a target tissue, the system comprising an endoscope comprising a light guide bundle comprising at least 100 light guides and having a proximal end and a distal end, the system further comprising a spatial light modulator that is optically connected to the proximal end of the light guide bundle in a same conjugate image plane as the proximal end such that the spatial light modulator controls the location of light impinging on the proximal end, and a controller comprising computer-implemented programming that is operably connected to the spatial light modulator and that is configured to set to an on-state groups of pixels of the spatial light modulator corresponding to cores of corresponding light guides in the light guide bundle to provide groups of on-pixels and configured to set to an off-state pixels corresponding to inter-core areas of the light guide bundle to provide off-pixels, wherein a plurality of selected groups of the on-pixels are in the on-state, the selected groups being spaced apart such that light emanating from the distal end of a first light guide corresponding to a first selected group of on-pixels does not substantially interfere with light emanating from the distal end of a second light guide corresponding to a second selected group of on-pixels, and other pixels of the spatial light modulator are in the off-state, wherein the endoscope further comprises a pixelated detector optically connected to receive light emanating from the proximal end of the light guide bundle and the controller further comprises computer-implemented programming that distinguishes between light emanating from the light guides corresponding to on-pixels of the spatial light modulator and light emanating from other light guides, and wherein the controller further comprises computer-implemented programming that detects light emanating from the other light guides to provide out-of-focus data and the programming incorporates the out-of-focus data with the light emanating from the light guides corresponding to the on-pixels to provide an enhanced image.

6. A method of obtaining an image of a target comprising:
a) transmitting light from a light source via a spatial light modulator to a light guide bundle, then emitting the light from a distal end of the light guide bundle to illuminate the target and thereby cause light to emanate from the target to provide emanating light;
b) collecting the emanating light that contacts the distal end of the light guide bundle; and
c) transmitting the emanating light via the light guide bundle to a detector to provide an image of the target at the detector, wherein the detector comprises an eyepiece ocular, wherein the detector comprises a pixelated detector, wherein the method comprises setting to an on-state pixels of the spatial light modulator that correspond to cores of corresponding light guides in the light guide bundle to provide on-pixels and setting to an off-state pixels corresponding to inter-core areas of the light guide bundle to provide off-pixels, wherein the method comprises setting a plurality of selected groups of the on-pixels to an on-state wherein the selected groups are spaced apart such that light emanating from the distal end of a first light guide corresponding to a first selected group of on-pixels does not substantially interfere in the target with light emanating from the distal end of at least one second light guide corresponding to at least one second selected group of on-pixels, and substantially all other pixels of the spatial light modulator are in the off-state to provide other light guides, and wherein the method further comprises evaluating the light emanating from the other light guides to provide out-of-focus data and the incorporating the out-of-focus data with the light emanating from the light guides corresponding to the on-pixels to provide an enhanced image.

* * * * *